United States Patent
Cha et al.

(10) Patent No.: US 9,801,972 B2
(45) Date of Patent: Oct. 31, 2017

(54) MUSSEL-INSPIRED BIOACTIVE SURFACE COATING COMPOSITION GENERATING SILICA NANOPARTICLES

(71) Applicant: POSTECH ACADEMY-INDUSTRY FOUNDATION, Pohang (KR)

(72) Inventors: Hyung Joon Cha, Pohang (KR); Yun Kee Jo, Pohang (KR); Hogyun Cheong, Pohang (KR); Changsup Kim, Pohang (KR); Bong-Hyuk Choi, Gyeongju (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 92 days.

(21) Appl. No.: 14/749,844

(22) Filed: Jun. 25, 2015

(65) Prior Publication Data

US 2016/0096868 A1    Apr. 7, 2016

(30) Foreign Application Priority Data

Oct. 2, 2014    (KR) .................. 10-2014-0133548
Nov. 25, 2014    (KR) .................. 10-2014-0165392

(51) Int. Cl.
| | | |
|---|---|---|
| *A61L 27/30* | (2006.01) | |
| *A61L 27/02* | (2006.01) | |
| *C07K 14/435* | (2006.01) | |
| *A61L 27/36* | (2006.01) | |
| *A61K 38/00* | (2006.01) | |

(52) U.S. Cl.
CPC ............. *A61L 27/025* (2013.01); *A61L 27/30* (2013.01); *A61L 27/3604* (2013.01); *C07K 14/43509* (2013.01); *A61K 38/00* (2013.01); *C07K 2319/00* (2013.01)

(58) Field of Classification Search
None
See application file for complete search history.

(56) References Cited

FOREIGN PATENT DOCUMENTS

| KR | 10-2016-0115115 | 10/2016 |
|---|---|---|
| WO | 2005/092920 | 10/2005 |
| WO | 2006/107183 | 10/2006 |

OTHER PUBLICATIONS

Kokubo, T, Kim, HM, Kawashita, M, "Novel bioactive materials with different mechanical properties", Jun. 2003. Biomaterials 24: 2161-2175.
Wong Po Foo, C, Huang, J, Kaplan, DL, "Lessons from seashells: silica mineralization via protein templating", Nov. 2004. Trends Biotechnol. 22: 577-585.
Bosetti, M, Cannas, M, "The effect of bioactive glasses on bone marrow stromal cells differentiation", Jun. 2005. Biomaterials 26: 3873-3879.
Caruso, RA, Antonietti, M, "Sol-Gel Nanocoating: An Approach to the Preparation of Structured Materials", Jul. 2001. Chem. Mater. 13: 3272-3282.
Fan, TX, Chow, SK, Zhang, D, "Biomorphic mineralization: From biology to materials", Jul. 2009, Prog. Mater. Sci. 54: 542-659.
Sumper, M, Kroger, N, "Silica formation in diatoms: the function of long-chain polyamines and silaffins", Apr. 2004, J. Mater. Chem. 14: 2059-2065.
Lee, BP, Messersmith, PB, Israelachivili, JN, Waite, JH, "Mussel-Inspired Adhesives and Coatings", Aug. 2011. Annu. Rev. Mater. Res. 41: 99-132.
Cha, HJ, Hwang, DS, Lim, S, "Development of bioadhesives from marine mussels", May 2008. Biotechnol. J. 3: 631-638.
Hwang, DS, Yoo, HJ, Jun, JH, Moon, WK, Cha, HJ, "Expression of Functional Recombinant Mussel Adhesive Protein Mgfp-5 in *Escherichia coli*", Jun. 2004. Appl. Environ. Microbiol. 70: 3352-3359.
Hwang, DS, Gim, Y, Yoo, HJ, Cha, HJ, "Practical recombinant hybrid mussel bioadhesive fp-151", Aug. 2007. Biomaterials 28: 3560-3568.
Cha, HJ, Hwang, DS, Lim, S, White, JD, Matos-Perez, CR, Wilker, JJ, "Bulk adhesive strength of recombinant hybrid mussel adhesive protein", Feb. 2009. Biofouling 25: 99-107.
Patwardhan, SV, Emami, FS, Berry, RJ, Jones, SE, Naik, RR, Deschaume, O, Heinz, H, Perry, CC, "Chemistry of Aqueous Silica Nanoparticle Surfaces and the Mechanism of Selective Peptide Adsorption", Mar. 2012. J. Am. Chem. Soc. 134: 6244-6256.
Hassert R et al., "Tuning peptide affinity for biofunctionalized surfaces", Eu. Jour. of Pharma. and Biophar. 85:pp. 69-77 (Feb. 27, 2013).
Tong Z et al., "Biomimetic and bioinspired synthesis of titania and titania-based materials", RSC Adv., pp. 12388-12403 (Feb. 19, 2014).

*Primary Examiner* — Anand Desai
(74) *Attorney, Agent, or Firm* — Lex IP Meister, PLLC

(57) ABSTRACT

The present invention relates to a fusion protein comprising a mussel adhesive protein and a silica-binding peptide linked to the mussel adhesive protein, a silica nanoparticle a silica connected to the fusion protein, a fusion protein-silica nanoparticle complex comprising the silica nanoparticle having bioactivity and adhesiveness for cell proliferation and accelerating the differentiation, a surface coating composition including the complex, its use, and a method of coating a surface using the surface coating composition.

7 Claims, 12 Drawing Sheets
(7 of 12 Drawing Sheet(s) Filed in Color)

MUSSEL-INSPIRED BIOACTIVE SURFACE COATING COMPOSITION GENERATING SILICA NANOPARTICLES

TECHNICAL FIELD

The present invention relates to a mussel-inspired bioactive surface coating composition generating silica nanoparticles, and use thereof, and more particularly, to a bioactive protein prepared by fusion of a recombinant mussel adhesive protein with a silica-binding peptide generating silica nanoparticles, a fusion protein-silica nanoparticle adhesive complex of the fusion protein and silica, and a method thereof, and a bioactive surface coating composition including the complex and a surface coating method.

BACKGROUND ART

Bone loss occurs in surgical treatment procedures such as orthopedic and dental surgery, traumatic injuries, or tumor removal, and implants and substitutes are widely used to restore areas of bone loss. In this regard, for successful in vivo repair, it is important to use a material capable of bearing loads of hard tissues and stimulating osteoprogenitor cells to induce bone regeneration (Kokubo, T, Kim, H-M, Kawashita, M, 2003. Biomaterials 24: 2161-2175).

Silica has been reported to play an important role in bone formation, because it has supporting and protecting functions, prevents penetration of connective tissue in the bone loss area, and stimulates expressions of osteogenic differentiation-related genes and cell proliferation (Wong Po Foo, C, Huang, J, Kaplan, D L, 2004. Trends Biotechnol. 22: 577-585).

With recent development of nanotechnology, many studies have been conducted to develop materials including silica-based nanoparticles, and they have been reported to have high bone regeneration effects (Bosetti, M, Cannas, M, 2005. Biomaterials 26: 3873-3879). For this reason, various medical biomaterials such as nanoscale silica-based coatings for implants or bone substitutes, catheters, dental materials and medical instrument may be used.

However, the silica nanoparticles have disadvantages that they are easily detached from the material surface when a widely used physical/chemical deposition method is used, and they require acidic or basic conditions and various chemical additives and thus are accompanied by a potential risk of toxicity when a sol-gel precipitation method is used. Further, a lithography method is problematic in that this method is limited to the target surface on which silica is formed, and is not suitable for in vivo environments (Caruso, R A, Antonietti, M, 2001. Chem. Mater. 13: 3272-3282). For this reason, there is an urgent need for a surface immobilization strategy which is biocompatible and effective for immobilization of silica nanoparticles on various surfaces.

Many organisms produce siliceous structures such as frustules in diatoms, spicules in sponges, and silica phytoliths in higher plants, which confer support and protection. Formation of the siliceous structures occurs in the organisms by particular proteins such as silicatein, silaffin, etc., and under environments similar to the biological conditions such as neutral pH, room temperature, etc. (Fan, T X, Chow, S K, Zhang, D, 2009. Prog. Mater. Sci. 54: 542-659).

In particular, R5 peptide which is a silica-binding peptide derived from a silaffin protein of the diatoms *Cylindrotheca fusiformis* induces and regulates silica formation under environments similar to the biological conditions so as to form silica nanoparticles (Sumper, M, Kroger, N, 2004, J. Mater. Chem. 14: 2059-2065).

Meanwhile, mussels, one of marine organisms, produce and secrete adhesive proteins that tightly attach themselves to wet solid surfaces such as underwater rocks, and thus they are not influenced by wave impact or buoyancy of seawater. Mussel adhesive proteins are known as a strong natural adhesive, and they exhibit about two times higher tensile strength than epoxy resin while having flexibility, compared to chemically synthesized adhesive (Lee, B P, Messersmith, P B, Israelachivili, J N, Waite, J H, 2011. Annu. Rev. Mater. Res. 41: 99-132).

Further, mussel adhesive proteins are able to adhere to various surfaces such as plastics, glass, metal, Teflon and biomaterials, and the like, and allow adhesion on wet surface within a few seconds, which remains an unsolved problem in development of chemical adhesives (Lee, B P, Messersmith, P B, Israelachivili, J N, Waite, J H, 2011. Annu. Rev. Mater. Res. 41: 99-132).

To obtain 1 gram of the adhesive material naturally extracted from mussels, however, about ten thousand of mussels are required. Therefore, despite very excellent physical properties of the mussel adhesive protein, there are many restrictions in industrial applications of the naturally extracted mussel adhesive proteins. As an alternative, a genetic recombination technology has been employed to mass-produce mussel adhesive proteins including Mefp (*Mytilus edulis* foot protein)-1, Mgfp (*Mytilus galloprovincialis* foot protein)-1, Mcfp (*Mytilus coruscus* foot protein)-1, Mefp-2, Mefp-3, Mgfp-3 and Mgfp-5, etc. (Cha, H J, Hwang, D S, Lim, S, 2008. Biotechnol. J. 3: 631-638; Hwang, D S, Yoo, H J, Jun, J H, Moon, W K, Cha, H J, 2004. Appl. Environ. Microbiol. 70: 3352-3359).

Mass-production of these recombinant mussel adhesive proteins is possible by using an *E. coli* expression vector, and these proteins are found to maintain adhesive strength of the existing mussel adhesive proteins (Hwang, D S, Gim, Y, Yoo, H J, Cha, H J, 2007. Biomaterials 28: 3560-3568; Cha, H J, Hwang, D S, Lim, S, White, J D, Matos-Perez, C R, Wilker, J J, 2009. Biofouling 25: 99-107).

However, there have been no reports about a mussel-inspired adhesive material, which is prepared by incorporating the recombinant mussel adhesive proteins having adhesion strength to various surfaces while being produced in a large amount with the silica nanoparticles.

DISCLOSURE

Technical Problem

An object of the present invention is to provide a fusion protein which is prepared by fusion of a silica-binding peptide to a mussel adhesive protein.

Another object of the present invention is to provide a fusion protein-silica nanoparticle complex for promoting tissue regeneration, which is prepared by incorporating the fusion protein of the mussel adhesive protein with the silica nanoparticles and the silica-binding peptide via the silica-binding peptide so as to have an adhesive property.

Still another object of the present invention is to provide a substrate surface coating composition, including the fusion protein-silica nanoparticle complex.

Still another object of the present invention is to provide a composition for promoting cell proliferation or differentiation, including the fusion protein-silica nanoparticle complex.

Still another object of the present invention is to provide a support for tissue engineering, including the fusion protein or the fusion protein-silica nanoparticle complex.

Still another object of the present invention is to provide a method for coating a substrate surface with the fusion protein or the fusion protein-silica nanoparticle complex.

Technical Solution

In an aspect to achieve the above objects, the present invention relates to a fusion protein, in which a silica-binding peptide is linked to a mussel adhesive protein.

In an embodiment, the mussel adhesive protein (MAP) is an adhesive protein derived from mussels, and preferably, it includes mussel adhesive proteins derived from *Mytilus edulis*, *Mytilus galloprovincialis*, or *Mytilus coruscus*, or variants thereof, but is not limited thereto.

For example, the mussel adhesive protein of the present invention includes fp (foot protein)-1 to fp-5 protein derived from the above mussel species, or variants thereof, and preferably, Mefp (*Mytilus edulis* foot protein)-1, Mgfp (*Mytilus galloprovincialis* foot protein)-1, Mcfp (*Mytilus coruscus* foot protein)-1, Mefp-2, Mefp-3, Mgfp-3 and Mgfp-5, or variants thereof, but is not limited thereto.

Further, the mussel adhesive protein of the present invention includes all mussel adhesive proteins described in International Patent Publication No. WO2006/107183 or WO2005/092920. Preferably, the mussel adhesive protein may include Mgfp-1 protein consisting of an amino acid sequence of SEQ ID NO. 1, Mgfp-5 protein consisting of an amino acid sequence of SEQ ID NO. 2, or variants thereof, but is not limited thereto.

Further, the mussel adhesive protein may include a polypeptide of 1 to 10 repeats of the fp-1 protein consisting of the amino acid sequence of SEQ ID NO. 1. Further, the mussel adhesive protein may include a fusion polypeptide of two or more selected from the group consisting of repeating polypeptides of SEQ ID NO. 1 and SEQ ID NO. 2, and preferably, the fusion polypeptide may be exemplified by fp-151 protein of SEQ ID NO. 3, but is not limited thereto. Most specifically, the mussel adhesive protein may be composed of any one of the amino acid sequences of SEQ ID NOS. 1 to 3 in the following Table 1.

TABLE 1

| SEQ ID NO. | Mussel adhesive protein | Amino acid sequence |
|---|---|---|
| 1 | fp-1 | AKPSYPPTYK |
| 2 | fp-5 | SEEYKGGYYPGNTYHYHSGGSYHGSGYHGGYKGKYYGKAKKYYYKYKNSGKYKYLKKARKYHRKGYKKYYGGSS |
| 3 | fp-151 | MAKPSYPPTYKAKPSYPPTYKAKPSYPPTYKAKPSYPPTYKAKPSYPPTYKAKPSYPPTYKPWSSEEYKGGYYPGNTYHYHSGGSYHGSGYHGGYKGKYYGKAKKYYYKYKNSGKYKYLKKARKYHRKGYKKYYGGSSGSAKPSYPPTYKAKPSYPPTYKAKPSYPPTYKAKPSYPPTYKAKPSYPPTYKAKPSYPPTYKL |

As used herein, the 'silica' may be a silica nanostructure which is mineralized using a silica precursor such as tetraethylorthosilicate (TEOS), tetramethylorthosilicate (TMOS), methyltrimethoxysilane (MTMS), or dimethyldimethoxysilane (DMS), and for example, tetramethylorthosilicate (TMOS) and tetraethyl orthosilicate (TEOS) may be used.

As used herein, the 'silica-binding peptide' may be R5 peptide capable of binding to silica, but the silica-binding peptide is not limited thereto, as long as it is a peptide capable of binding to silica particles that improve bioactivity (Patwardhan, S V, Emami, F S, Berry, R J, Jones, S E, Naik, R R, Deschaume, O, Heinz, H, Perry, C C, 2012. J. Am. Chem. Soc. 134: 6244-6256), and specifically, as in the following Table 2. Particularly, the silica-binding peptide may be one or more selected from the group consisting of amino acid sequences of SEQ ID NOS. 4 to 7.

TABLE 2

| SEQ ID NO. | Peptide | Amino acid sequence |
|---|---|---|
| 4 | R5 | SSKKSGSYSGSKGSKRRIL |
| 5 | pep1 | KSLSRHDHIHHH |
| 6 | Si4-1 | MSPHPHPRHHHT |
| 7 | Si4-10 | RGRRRLSCRLL |

Specifically, the mussel adhesive protein in the complex may be also a protein of 1 to 10 repeats of the amino acid sequence of SEQ ID NO. 1, a protein consisting of the amino acid sequence of SEQ ID NO. 3, or a protein consisting of the amino acid sequence of SEQ ID NO. 2, but is not limited thereto.

More specifically, the silica-binding peptide is linked to the mussel adhesive protein to form silica nanoparticles, which may be a complex for improving bioactivity. The silica-binding peptide may be a peptide consisting of the amino acid sequence of SEQ ID NO. 5.

In an embodiment of the present invention, bioactive effects of the complex, in which silica nanoparticles are formed, were examined. Specifically, the complex was found to exhibit excellent bioactive effects of promoting tissue regeneration, including cell attachment, proliferation, spreading, and differentiation (FIGS. 10 to 14).

Specifically, in the present invention, a nanofiber based on the fusion protein linked with the silica-binding peptide was prepared by an electrospinning process, and as shown in FIGS. 15 and 16, silica nanoparticles were formed on the surface of the nanofiber.

The fusion protein of the present invention may be mixed with a polymer to prepare a synthetic polymer solution, and then the electrospinning process may be performed to prepare the nanofiber. The polymer may include most biodegradable polymers.

For example, the polymer may be exemplified by polycaprolactone (PCL), polydioxanone (PDO), poly(L-lactide), PLLA) and poly(DL-lactide-co-glycolide) (PLGA) which are known to be dissolved in an HFIP solvent and well achieve electrospinning, and PEO (polyethylene oxide) and PVA (polyvinyl alcohol) which are known to be water-soluble.

The electrospinning process is a technology of forming a fiber using attractive force and repulsive force generated when a polymer solution or a molten polymer is charged to a predetermined voltage. According to the electrospinning process, fibers with various diameters including several nm to several thousand nm may be prepared, the structure of the equipment is simple, it may be applied for various materials, and porosity may be increased compared to existing fibers, thus enabling preparation of a fiber having a large ratio of surface area to volume.

Furthermore, the fusion protein and the biodegradable polymer may be mixed at various ratios to prepare a nanofiber by electrospinning. For example, the biodegradable polymer and the fusion protein are mixed at a ratio of 90:10 to 10:90, preferably, 80:20 to 70:30 (w/w), and more preferably, 50:50 (w/w) and then, electrospinning is conducted to prepare the nanofiber.

Further, the nanofiber is immersed in a solution containing ionized silica so as to form silica nanoparticles on the surface.

The present invention relates to a substrate surface coating composition, including the fusion protein-silica nanoparticle complex for promoting tissue regeneration.

Specifically, the substrate may be a medical device selected from the group consisting of stents, artificial valves, implants, implant supports, and medical setscrews, or it may be polymer compounds, metals and glasses. The polymer compound may include polystyrene, polyethylene, polyacrylonitrile, polymethyl methacrylate, collagen, chitosan, alginic acid, and hyaluronic acid, and the metal may include titanium, aluminum, and stainless steel.

In another aspect, the present invention relates to a method for preparing the fusion protein-silica nanoparticle complex for promoting tissue regeneration, including the step of immersing the fusion protein containing the mussel adhesive protein and the silica-binding peptide in a solution containing silica ions so as to form silica nanoparticles on the silica-binding peptide.

More specifically, the fusion protein-silica nanoparticle complex for promoting tissue regeneration may be a protein-oxide nanoparticle complex that includes the fusion protein formed by linking the silica-binding peptide to the mussel adhesive protein, and silica nanoparticles formed by linking silica components to the silica-binding peptide of the fusion protein, and has bioactivity and adhesiveness, or a nanofiber prepared by spinning the fusion protein alone or a mixture of the fusion protein and one polymer selected from the group consisting of polycaprolactone (PCL), polydioxanone (PDO), poly(L-lactide) (PLLA), poly(DL-lactide-co-glycolide) (PLGA), polyethylene oxide (PEO) and polyvinyl alcohol (PVA).

In still another aspect, the present invention relates to a method for coating the substrate surface, including the steps of adhering the fusion protein, which is prepared by linking the silica-binding peptide to the mussel adhesive protein, onto the surface of a subject to be coated; and linking silica to the surface onto which the fusion protein is adhered, so as to form silica nanoparticles.

Specifically, the complex may be a nanofiber which is prepared by spinning the fusion protein alone or a mixture of the fusion protein and one polymer selected from the group consisting of polycaprolactone (PCL), polydioxanone (PDO), poly(L-lactide) (PLLA), poly(DL-lactide-co-glycolide) (PLGA), polyethylene oxide (PEO) and polyvinyl alcohol (PVA).

In still another aspect, the present invention relates to a support for tissue engineering, of which surface is coated with the coating composition including the fusion protein-silica nanoparticle complex for promoting tissue regeneration.

The tissue engineering may be applied for regeneration of most organs of human body including artificial skin, artificial cartilage, artificial bone, artificial vessel, artificial muscle, and the like, and it is important to form a support which is non-toxic to cells and has physical properties similar to real tissues.

The fusion protein of the mussel adhesive protein and the silica-binding peptide, or the complex prepared by linking silica nanoparticles to the fusion protein of the present invention provides a tissue-like support that functions to restore tissue defects as well as to promote regeneration of tissues and organs in tissue engineering.

The cells may be all cells including prokaryotic and eukaryotic cells, and exemplified by fibroblasts, osteoblasts, neurons, immune cells such as B cells, and embryonic cells.

Effect of the Invention

In the present invention, silica nanoparticles are allowed to be linked to the mussel adhesive protein, which can be used as a coating composition having bioactive effects of promoting cell proliferation or differentiation, and there is an advantage that it can be used to coat various surfaces without limitation to the type of the surface due to excellent adhesive strength of the mussel adhesive protein.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE EMBODIMENTS

Hereinafter, the present invention will be described in detail with reference to Examples. However, these Examples are for illustrative purposes only, and the invention is not intended to be limited by these Examples.

Example 1. Preparation of Fusion Protein

Primers (Table 3) for a silica-binding peptide sequence derived from the diatoms *C. fusiformis* were constructed. These primers were used to perform polymerase chain reaction, thereby preparing a fusion protein, in which the silica-binding peptide was linked to a mussel adhesive protein, fp-1 (SEQ ID NO. 1) or fp-151 (SEQ ID NO. 3).

TABLE 3

| SEQ ID NO. | Primer | Nucleotide sequence (5'→3') |
|---|---|---|
| 8 | Forward for R5 | GCGCCATATGAGCAGCAAAAAATCTGGCTCCTATT CAGGCTCGAAAGGTTCTAAACGTCGCATTCTGGGT GGCGGAGGGGCGAAACCGAGCTATCCGCCGACC |
| 9 | Reverse for MAP | GCGCCTCGAGCTTGTACGTTGGAGGATAAGAAGG |

Figure 1:
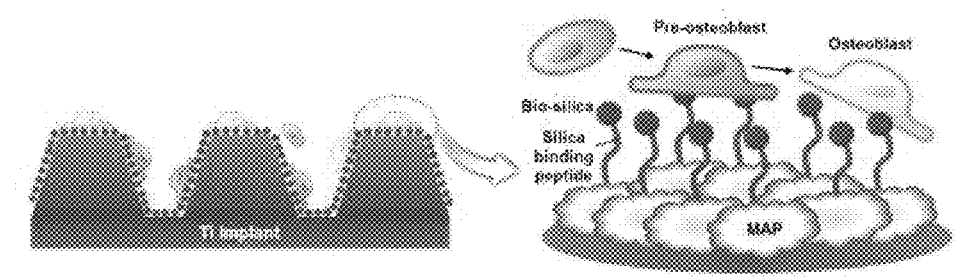
FIG. 1 is a schematic illustration showing bioactive effects, in which the surface of titanium implant is coated with silica nanoparticles and osteoblasts are bound thereon according to an embodiment of the present invention.
Figure 2:
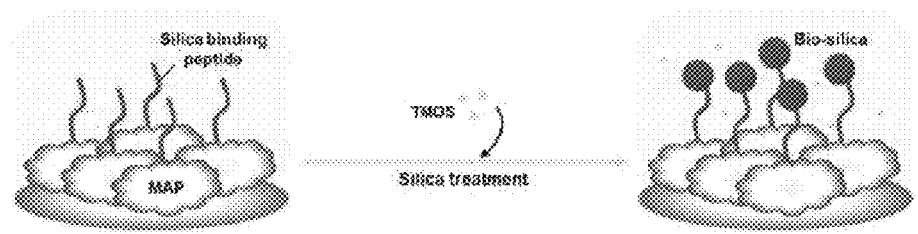
FIG. 2 is a schematic illustration showing a formation process of silica nanoparticles by coating a substrate surface with a mussel adhesive protein-based fusion protein according to an embodiment of the present invention.
Figure 3:
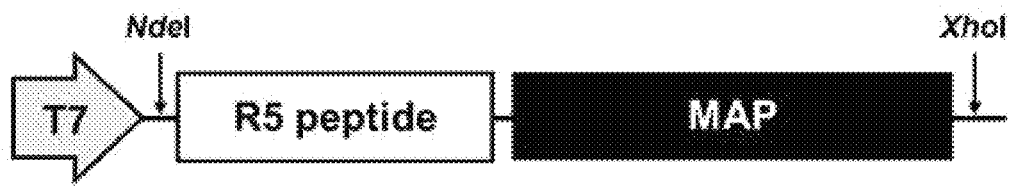
FIG. 3 is a schematic illustration of a vector for preparing an R5-MAP fusion protein according to an embodiment of the present invention.

As in FIG. 3 showing the schematic illustration of fusion protein (R5-MAP) construction, an R5 peptide (SEQ ID NO. 5; SSKKSGSYSGSKGSKRRIL) was linked to a mussel adhesive protein (MAP), such as mussel adhesive protein fp-1 or fp-151. A pET-22b(+) vector containing T7 promoter was used as a plasmid vector, and transformed into an *E. coli* TOP10 strain. Further, for expression of the fusion protein, the cloned recombinant vector was further transformed into an *E. coli* BL21 (DE3) strain.

*E. coli* transformed with the nucleotide sequence encoding the R5-MAP fusion protein was cultured in an LB liquid medium containing 50 µg/ml of ampicillin at 37° C., 300 rpm, and when optical density at 600 nm (OD600) reached 0.4 to 0.6, 1 mM isopropyl-β-D-thiogalactopyranoside (IPTG) was added thereto, followed by incubation for 8 hours under the same conditions. The cells thus cultured were centrifuged at 4° C., 18,000×g for 10 minutes, and a cell pellet was resuspended in an elution buffer (10 mM Tris-HCl, and 100 mM sodium phosphate, pH 8) and disrupted under 200 Kpsi. To obtain cell debris from the resulting cell lysate, centrifugation was performed at 4° C., 18,000×g for 20 minutes and a desired fusion protein was extracted using 25% (v/v) acetic acid. The fusion protein finally purified was freeze-dried and stored at −80° C.

Figure 4:
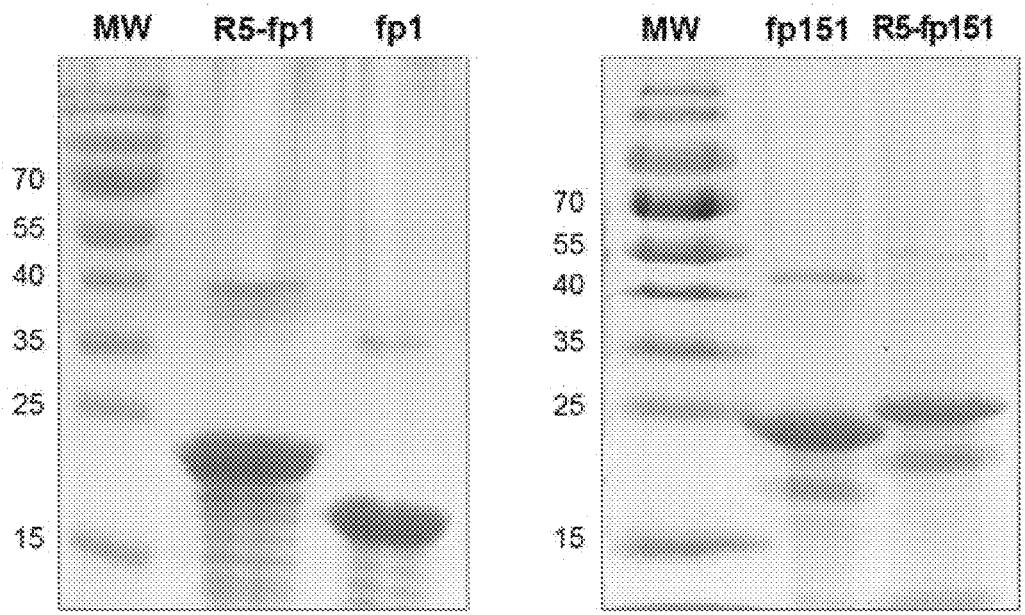
FIG. 4 shows the result of SDS-PAGE for examining expression of the R5-MAP fusion protein according to an embodiment of the present invention.

Production and purification of the respective proteins were analyzed by 12% (w/v) SDS-PAGE, and successful expression of the fusion proteins was examined by electrophoresis. The result of the electrophoresis is shown in FIG. 4. The concentrations of the fusion proteins were determined by Bradford assay (Bio-Rad).

Example 2. Preparation of Fusion Protein-Silica Nanoparticle Complex 2-1: Use of Polymer Substrate Surface To coat the surface of a coverslip made of polystyrene with the fusion protein-silica nanoparticle complex, 5% acetic acid solution containing 5 mg/ml of the fusion protein prepared in Example 1 was applied to the substrate surface, and left at room temperature for 12 hours to perform protein deposition. In this regard, to remove the fusion proteins which were not properly adhered to the surface, the substrate surface was washed with distilled water so as to obtain a fusion protein (R5-MAP)-coated substrate surface.

The fusion protein-coated substrate surface was immersed in 1 M trimethylorthosilicate (TMOS) solution for 2 minutes so as to prepare a complex, in which the silica nanoparticles were linked to the fusion protein. To remove silica which was not properly adhered to the substrate surface, the substrate surface was washed with distilled water.

Figure 5:
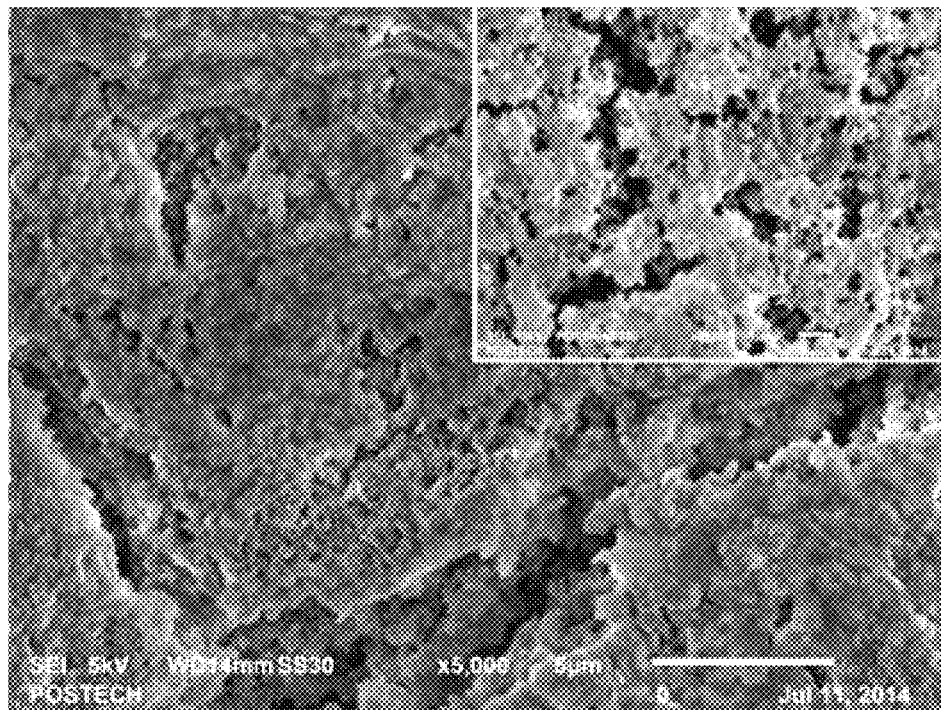
FIG. 5 shows the shape of silica nanoparticles, examined by scanning electron microscopy (SEM) of a fusion protein-silica nanoparticle complex coated on the surface of a polymer according to an embodiment of the present invention.

To confirm formation of the fusion protein-silica nanoparticle complex (Si-R5-MAP) and to examine shape of the complex, scanning electron microscopy (SEM) was performed and the resulting SEM images are shown in FIG. 5.

FIG. 5 shows scanning electron microscopic image (SEM) of the protein-silica nanoparticle complex coated on the surface of the polymer. As shown in FIG. 5, particles which were formed on the surface coated with R5-MAP fusion protein were found to have a size of about 100 nm and to be spherical silica particles.

2-2: Use of Metal Substrate Surface

Titanium, aluminium, and stainless steel surfaces were coated with the fusion protein prepared in Example 1 in the substantially same manner as in Example 2-1, and each of the substrate surfaces coated with the fusion protein was linked with silica using 1 M trimethylorthosilicate (TMOS) solution to prepare a fusion protein-silica nanoparticle complex (Si-R5-MAP).

The surfaces were analyzed by SEM photography. The result of forming the fusion protein-silica nanoparticle complex (Si-R5-MAP) on the titanium surface is shown in FIG. 6, the result of forming the fusion protein-silica nanoparticle complex (Si-R5-MAP) on the aluminium surface is shown in FIG. 7, and the result of forming the fusion protein-silica nanoparticle complex (Si-R5-MAP) on the stainless steel surface is shown in FIG. 8.

Figure 6:
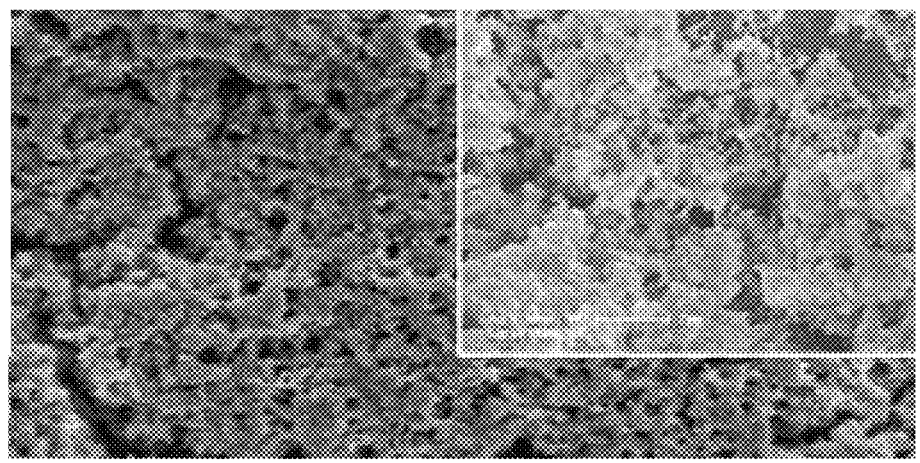
FIG. 6 shows a scanning electron microscopic image (SEM) of the fusion protein-silica nanoparticle complex coated on the surface of titanium according to an embodiment of the present invention.
Figure 7:
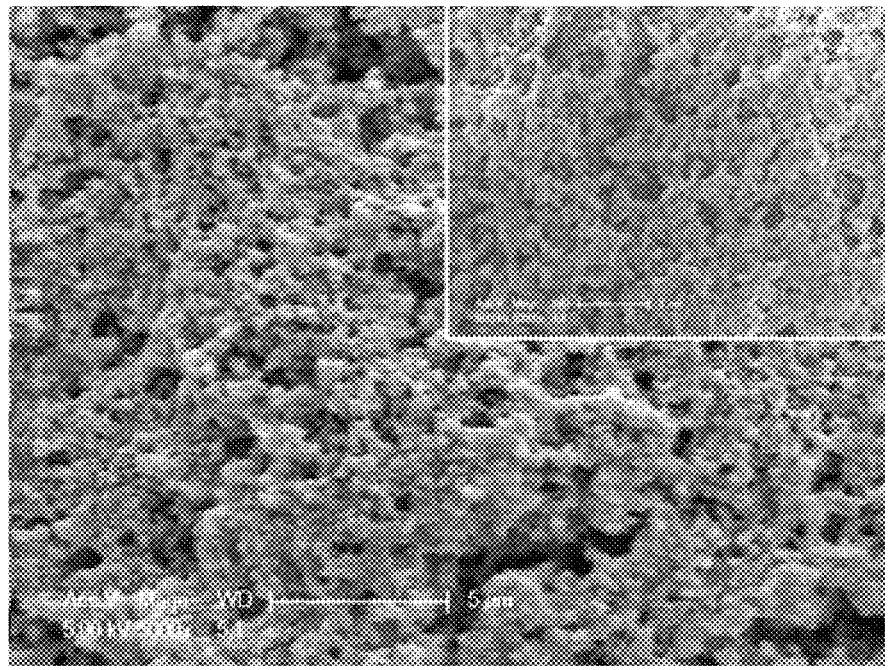
FIG. 7 shows a scanning electron microscopic image (SEM) of the fusion protein-silica nanoparticle complex coated on the surface of aluminium according to an embodiment of the present invention.
Figure 8:
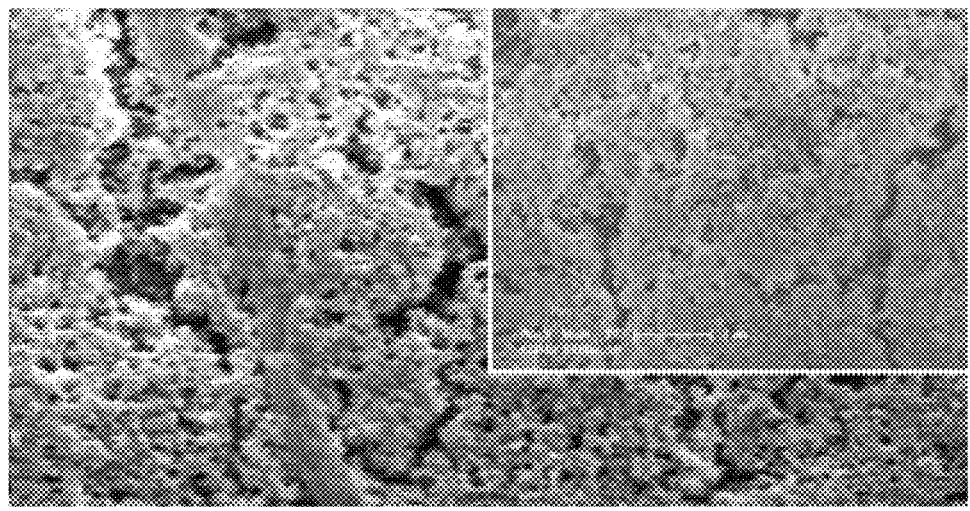
FIG. 8 shows a scanning electron microscopic image (SEM) of the fusion protein-silica nanoparticle complex coated on the surface of stainless steel according to an embodiment of the present invention.

As shown in FIGS. 6 to 8, it was found that after R5-MAP fusion proteins were successfully coated onto the titanium, aluminium, and stainless steel surfaces, silica nanoparticles were formed by TMOS solution.

2-3: Elementary Analysis of Silica on Coating Surface

Figure 9:
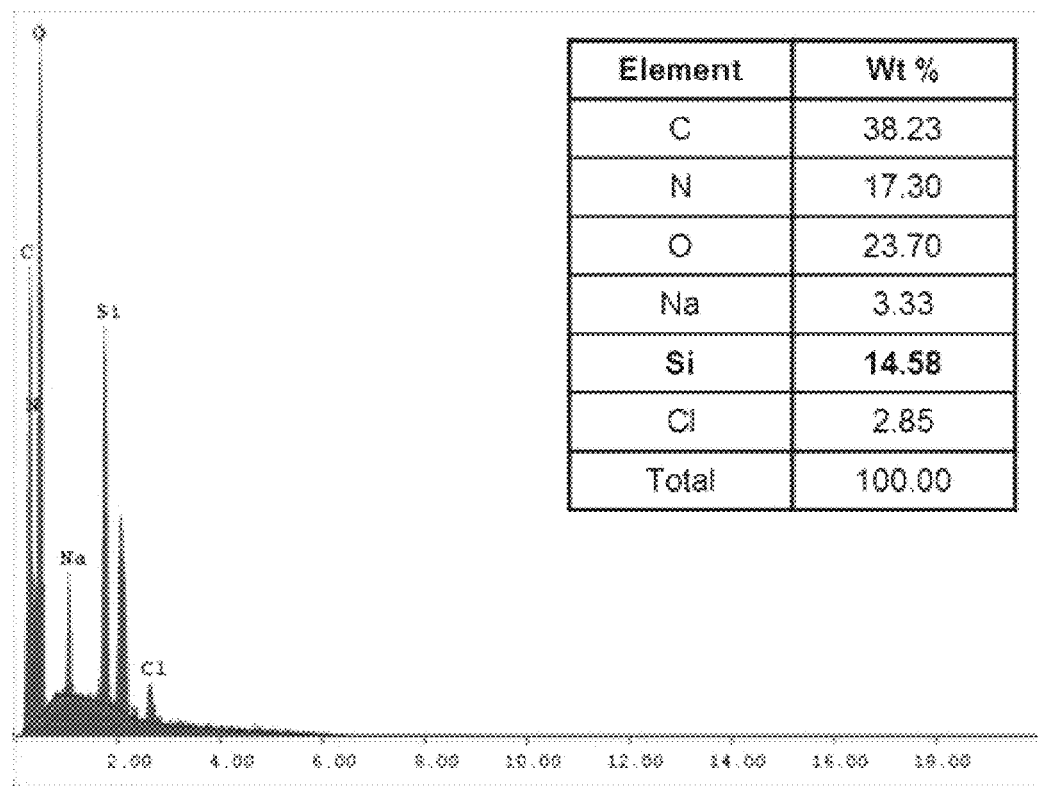
FIG. 9 shows formation of silica nanoparticles, examined by energy dispersion X-ray spectroscopy (EDS) of the fusion protein-silica nanoparticle complex coated on the substrate surface according to an embodiment of the present invention.

To analyze the structure of the coating surface of the substrate obtained in Example 2-1, energy dispersion X-ray spectroscopy (EDS) was performed, and the result is shown in FIG. 9.

FIG. 9 shows formation of silica nanostructure, examined by energy dispersion X-ray spectroscopy (EDS). As shown in FIG. 9, the elemental composition of particles was examined by energy dispersion X-ray spectroscopy (EDS), and as a result, the element constituting the produced nanoparticles was found to be silica.

Example 3. In Vitro Cell Test of Surface Coating Composition 3-1: Cell Culture by Use of Surface Coating Composition A cell function-improving ability of the bioactive surface coating composition including the fusion protein-silica nanoparticle complex of Example 2 was examined in vitro.

In the same manner as in Example 2-1, four types of the coated substrate surfaces were prepared by coating the surface of the polystyrene coverslip. In detail, the four types of the coated substrate surfaces include 1) the surface of polystyrene coverslip (NC) which was coated with none of the fusion protein and TMOS, 2) the surface (Si—NC) which was coated with TMOS, but without R5-MAP fusion protein, 3) the surface (R5-MAP) which was coated without TMOS, but with R5-MAP fusion protein, and 4) the surface (Si-R5-MAP) which was coated with R5-MAP fusion protein-silica nanoparticle complex formed after treatment of TMOS solution.

$5 \times 10^4$ mouse osteoblast MC3T3-E1 cells were cultured on the four surfaces thus prepared.

3-2: Test of Cell Adhesion and Proliferation by Optical Density

As a result of cell culture, 3) the surface (R5-MAP) which was coated without TMOS, but with R5-MAP fusion protein, and 4) the surface (Si-R5-MAP) which was coated with R5-MAP fusion protein-silica nanoparticle complex formed after treatment of TMOS solution showed higher cell adhesion and proliferation than 1) the surface of polystyrene coverslip (NC) which was coated with none of the fusion protein and TMOS, 2) the surface (Si—NC) which was coated with TMOS, but without R5-MAP fusion protein, and 4) the surface (Si-R5-MAP) which was coated with R5-MAP fusion protein-silica nanoparticle complex formed after treatment of TMOS solution showed more excellent cell proliferation effects.

Mouse osteoblasts were cultured on the four surfaces for 72 hours, and then optical density thereof was measured. The results are shown in FIGS. 10 and 11.

Figure 10:
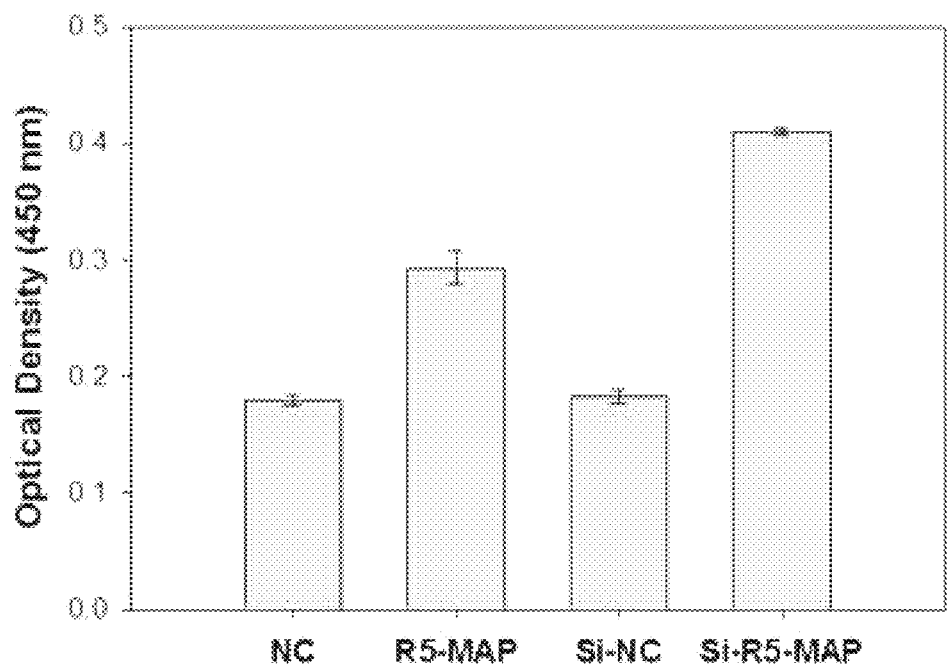
FIG. 10 is a graph showing adhesion of mouse osteoblasts onto the respective surfaces of a material coated with no fusion protein, a material coated with non-TMOS treated R5-MAP fusion protein, and a material coated with R5-MAP fusion protein-silica nanoparticle complex formed after treatment of TMOS solution.

FIG. 10 is a graph showing adhesion of mouse osteoblasts onto the respective surfaces of a material coated with no fusion protein, a material coated with non-TMOS treated R5-MAP fusion protein, and a material coated with R5-MAP fusion protein-silica nanoparticle complex formed after treatment of TMOS solution. FIG. 11 is a graph showing proliferation of mouse osteoblasts on the respective surfaces of the material coated with no fusion protein, the material coated with non-TMOS treated R5-MAP fusion protein, and the material coated with R5-MAP fusion protein-silica nanoparticle complex formed after treatment of TMOS.

Figure 11:
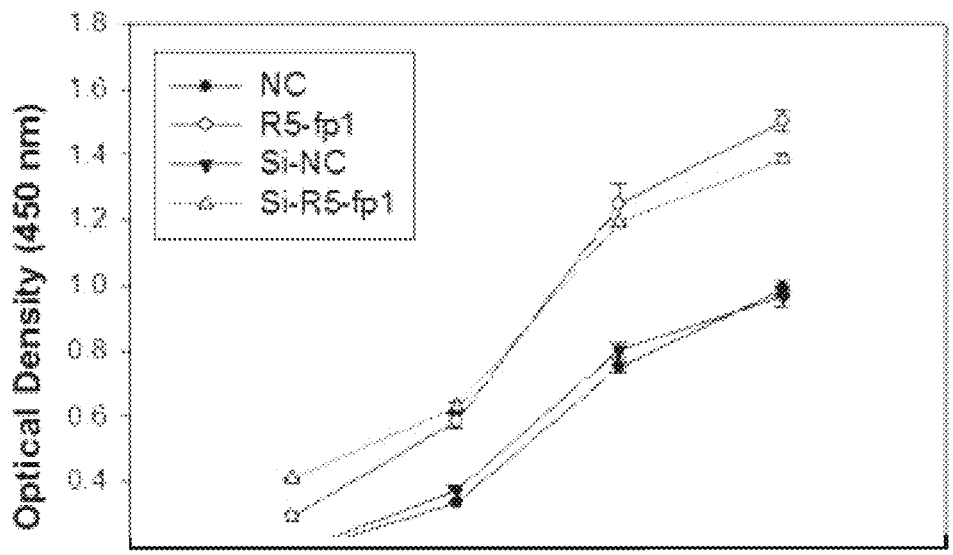
FIG. 11 is a graph showing proliferation of mouse osteoblasts on the respective surfaces of the material coated with no fusion protein, the material coated with non-TMOS treated R5-MAP fusion protein, and the material coated with R5-MAP fusion protein-silica nanoparticle complex formed after treatment of TMOS.

The R5-MAP protein itself and silica nanoparticle were found to slightly affect cell proliferation and adhesion (FIGS. 10 and 11).

3-3: Test of Cell Spreading by Fluorescence Staining

Figure 12:
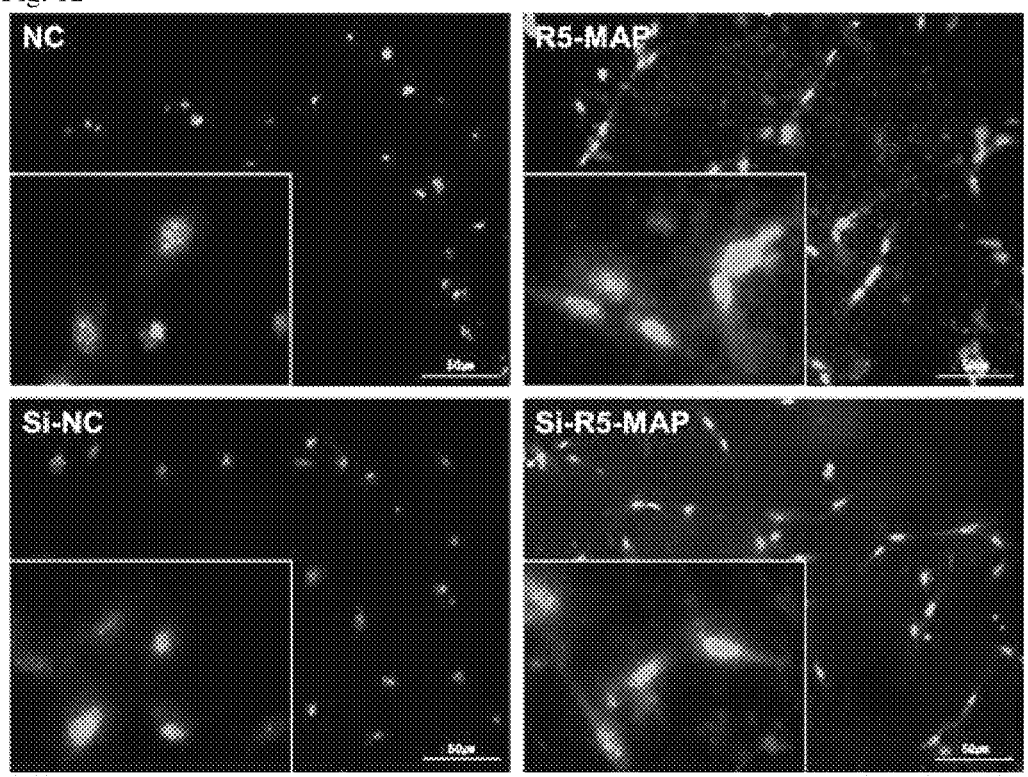
FIG. 12 shows DAPI and FITC fluorescence images for analyzing spreading of mouse osteoblasts on the respective surfaces of the material coated with no fusion protein, the material coated with non-TMOS treated R5-MAP fusion protein, and the material coated with R5-MAP fusion protein-silica nanoparticle complex formed after treatment of TMOS.

Mouse osteoblasts were cultured on the four surfaces for 1 day, and then fluorescence staining was performed. The result is shown in FIG. 12. FIG. 12 shows DAPI and FITC fluorescence images for analyzing spreading of mouse osteoblasts on the respective surfaces of the material coated with no fusion protein, the material coated with non-TMOS treated R5-MAP fusion protein, and the material coated with R5-MAP fusion protein-silica nanoparticle complex formed after treatment of TMOS.

As shown in FIG. 12, fluorescence staining was performed after culturing mouse osteoblasts for 1 day on the surface of polystyrene coverslip on which silica nanoparticles were formed by treatment of TMOS solution after coating with R5-MAP fusion protein. As a result, long cell spreading was observed on the surface on which silica was formed, and the R5-MAP coating surface on which no silica was formed due to non-treatment of TMOS solution, compared to a control surface, indicating that the R5-MAP protein itself and silica nanoparticle affect cell shape.

3-4: Test of Cell Proliferation by Alizarin Red S Staining

Figure 13:
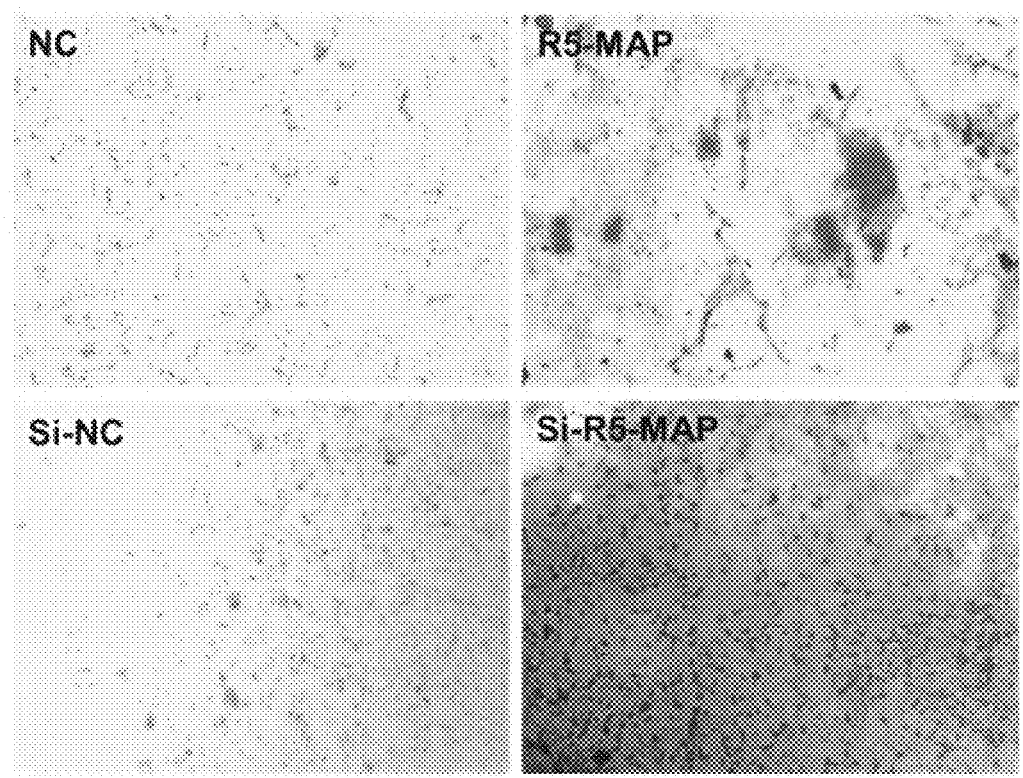
FIG. 13 shows alizarin-red S staining images for analyzing differentiation of mouse osteoblasts on the respective surfaces of the material coated with no fusion protein, the material coated with non-TMOS treated R5-MAP fusion protein, and the material coated with R5-MAP fusion protein-silica nanoparticle complex formed after treatment of TMOS.

To examine cell proliferation patterns, mouse osteoblasts were cultured on the four surfaces for 15 days, and then alizarin red S staining was performed. The result is shown in FIG. 13. The alizarin red S staining is one of the most frequently used methods to evaluate mineralization of bone matrix, and mineralization of bone matrix is known as an indicator of osteoblasts. In detail, the cultured osteoblasts were washed with phosphate buffered saline and fixed with 4% formaldehyde for 10 minutes. The cells were stained with 2% alizarin red S under gentle shaking for 5 minutes, and then washed with desalted water several times to remove the remaining staining solution. Staining patterns were observed.

FIG. 13 shows alizarin-red S staining images for analyzing differentiation of mouse osteoblasts on the respective surfaces of the material coated with no fusion protein, the material coated with non-TMOS treated R5-MAP fusion protein, and the material coated with R5-MAP fusion protein-silica nanoparticle complex formed after treatment of TMOS.

As shown in FIG. 13, to examine cell differentiation patterns on the surface of polystyrene coverslip on which silica nanoparticles were formed by treatment of TMOS solution after coating with R5-MAP fusion protein, mouse osteoblasts were cultured for 15 day and then alizarin red S staining was performed. As a result, the surface on which silica was formed was stained in red color, compared to the control surfaces (NC and Si—NC).

3-5: Test of Calcium Deposition

Figure 14:
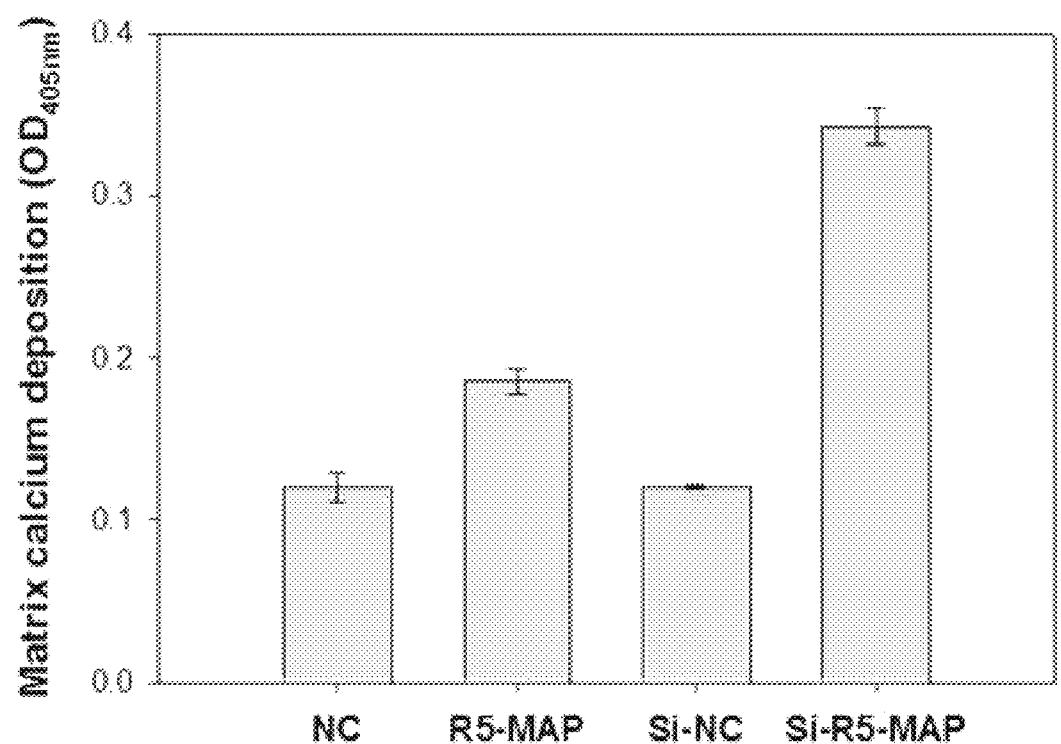
FIG. 14 shows the result of quantifying calcium deposition for analyzing intracellular calcium deposition ability as a result of differentiation of mouse osteoblasts on the respective surfaces of the material coated with no fusion protein, the material coated with non-TMOS treated R5-MAP fusion protein, and the material coated with TMOS-treated R5-MAP fusion protein-silica nanoparticle complex.

The cells proliferated on the four surfaces were treated with 10% acetic acid to obtain calcium. The amount of calcium was measured and the result is shown in FIG. 14. FIG. 14 shows the result of quantifying calcium deposition for analyzing intracellular calcium deposition ability as a result of differentiation of mouse osteoblasts on the respective surfaces of the material coated with no fusion protein, the material coated with non-TMOS treated R5-MAP fusion protein, and the material coated with R5-MAP fusion protein-silica nanoparticle complex formed after treatment of TMOS.

As shown in FIG. 14, calcium was eluted with 10% acetic acid and staining degree was quantified. As a result, higher production of calcium in the matrix was observed on the surface, on which silica was formed, compared to the control surface. 3) The surface (R5-MAP) which was coated without TMOS, but with R5-MAP fusion protein, and 4) the surface which was coated with R5-MAP fusion protein-silica nanoparticle complex formed after treatment of TMOS solution showed a large amount of calcium deposition in the matrix which is a late stage indicator of osteogenic differentiation, compared to the control groups, 1) the surface of polystyrene coverslip (NC) which was coated with none of the fusion protein and TMOS and 2) the surface (Si—NC) which was coated with TMOS, but without R5-MAP fusion protein. Further, 4) the surface which was coated with R5-MAP fusion protein-silica nanoparticle complex showed a better result than 3) the surface which was coated with only R5-MAP fusion protein. Consequently, it was confirmed that the R5-MAP protein itself and silica nanoparticle are effective for cell differentiation.

Example 4. Preparation of Surface Coating Composition by Use of Nanofiber 4-1: Coating Composition Using Nanofiber of Fusion Protein The R5-MAP fusion protein and a synthetic polymer PCL (polycaprolactone) solution were blended and used in an electrospinning process.

In detail, for electrospinning, the fusion protein prepared in Example 1 and polycaprolactone (PCL) were dissolved in hexafluoroisopropanol (HFIP) at a concentration of 6.5 wt %, respectively. Thereafter, the polycaprolactone (PCL) solution and the R5-MAP fusion protein solution were mixed at a ratio of 5:5, and subjected to electrospinning in a 5 ml-syringe having a needle diameter of 0.4 mm at a mass flow rate of 0.3 ml/h. In this regard, while high voltage (8 to 10 kV) was applied to the tip of the needle of the syringe, a nanofiber was produced. The produced nanofiber was randomly collected on the aluminum foil which was set at 10 cm distance from the tip of the needle. The produced nanofiber was shown in FIG. 15.

Figure 15:
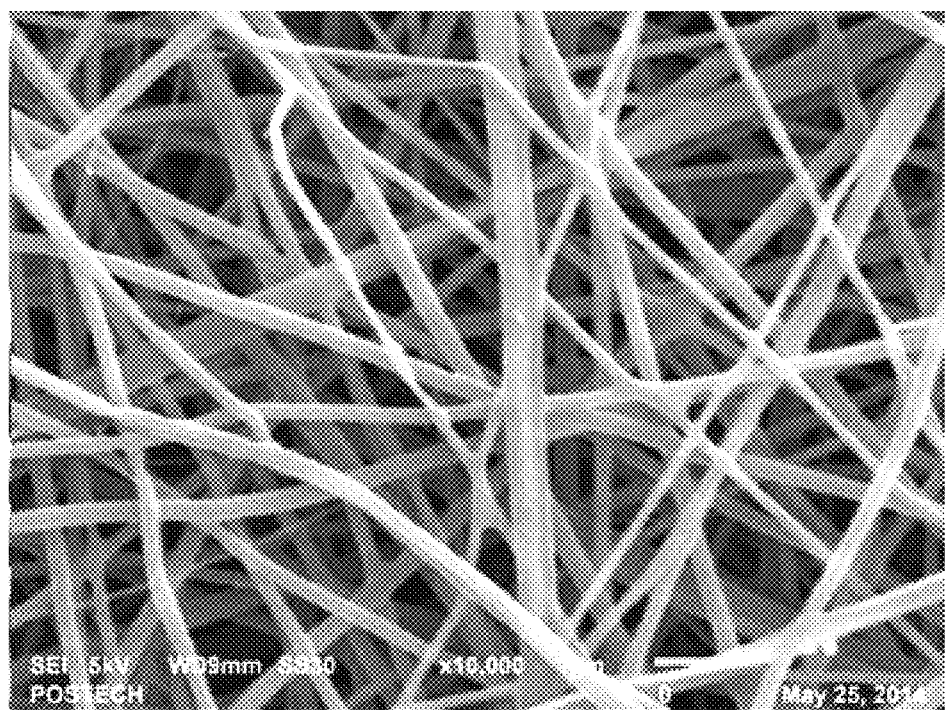
FIG. 15 shows an R5-MAP fusion protein-based nanofiber (R5-MAP/PCL mixture, 50:50 (w/w))

FIG. 15 shows an R5-MAP fusion protein-based nanofiber (R5-MAP/PCL mixture, 50:50 (w/w)).

4-2: Coating Composition Using Nanofiber of Fusion Protein-Silica Nanoparticle Complex The fusion protein (R5-MAP) nanofiber prepared in Example 4-1 was dried under vacuum for at least 3 days to remove the remaining solution.

The dried R5-MAP nanofiber was treated in the TMOS solution for about 30 seconds to bind the silica nanoparticles on the fiber surface, thereby preparing a nanofiber of the fusion protein-silica nanoparticle complex. A photograph of the nanofiber of the fusion protein-silica nanoparticle complex thus obtained is shown in FIG. 15.

Figure 16:
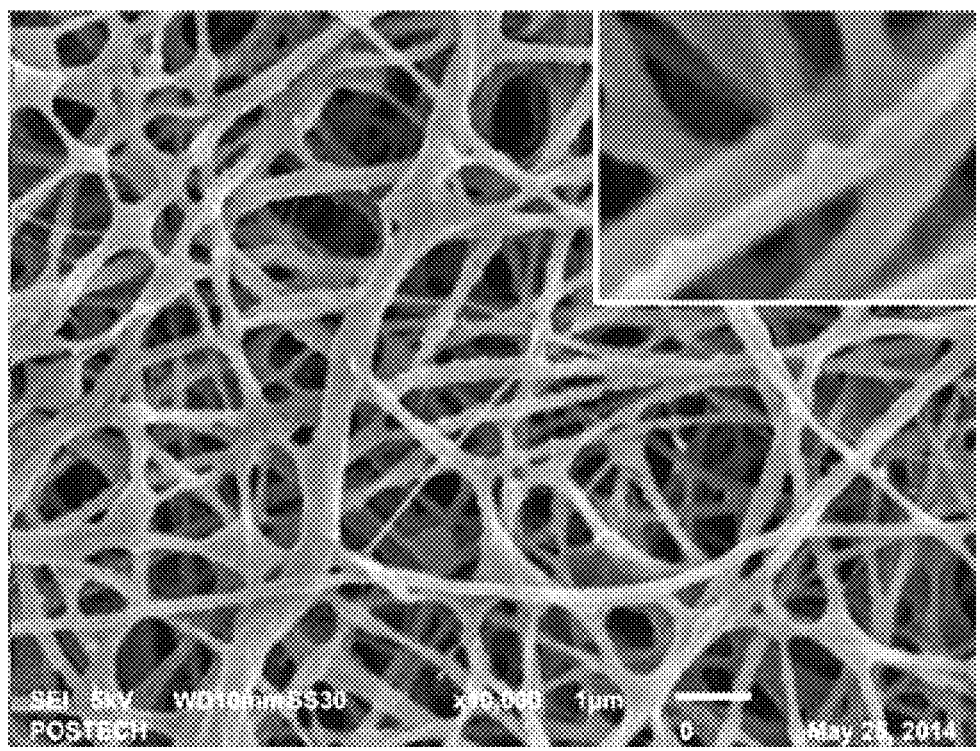
FIG. 16 shows formation of silica nanoparticles on the surface of the nanofiber after treatment of the R5-MAP fusion protein-based nanofiber (R5-MAP/PCL mixture, 50:50 (w/w)) with a TMOS solution.

FIG. 16 shows formation of silica nanoparticles on the surface of the nanofiber by treatment of the R5-MAP fusion protein-based nanofiber (R5-MAP/PCL mixture, 50:50 (w/w)) with TMOS solution.

4-3: Elementary Analysis of Silica on Coating Surface

Figure 17:
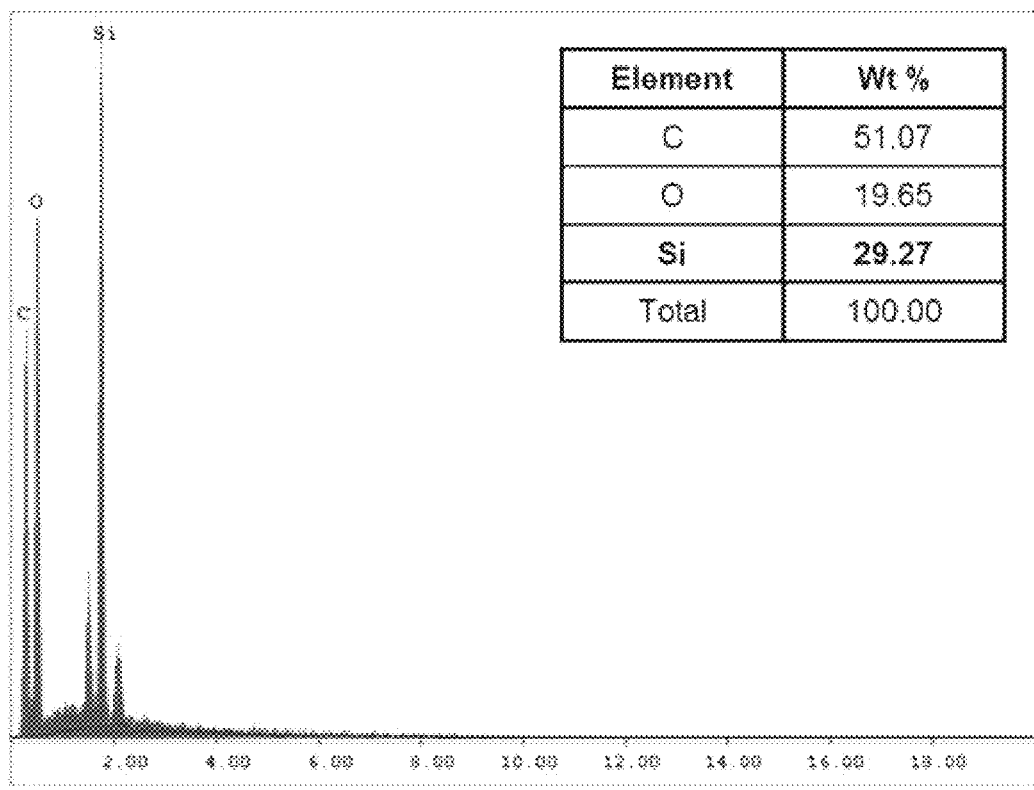
FIG. 17 shows formation of silica nanoparticles on the surface of the nanofiber, examined by energy dispersion X-ray spectroscopy (EDS).

The complex nanofiber including silica nanoparticles bound to the fusion protein (R5-MAP) nanofiber in Example 4-1 was subjected to energy dispersion X-ray spectroscopy (EDS), and the result is shown in FIG. 17. FIG. 17 shows formation of silica nanostructure, examined by energy dispersion X-ray spectroscopy (EDS).

As shown in FIG. 17, the surface elemental analysis by EDS showed that the formed silica occupied about 29% of the surface. Consequently, prepared was a nanofiber which was coated with the surface coating composition including the fusion protein-silica nanoparticle complex for promoting tissue regeneration of the present invention.

What is claimed is:

1. A method for promoting osteoblast attachment, proliferation, spreading and differentiation including the steps of
   providing a substrate;
   coating the substrate with a substrate surface coating composition comprising a fusion protein comprising a mussel adhesive protein and a silica-binding peptide linked to the mussel adhesive protein; and
   providing osteoblast on the substrate surface coating composition so as to promote the attachment, proliferation, spreading and differentiation of the osteoblast.

2. The method according to claim 1, additionally including a step of linking silica to the substrate onto which the fusion protein is adhered so as to form a fusion protein-silica nanoparticle complex.

3. The method according to claim 1, wherein the substrate is polymer, metal or glass.

4. The method according to claim 1, wherein the substrate is a medical device selected from the group consisting of stents, artificial valves, implants, implant supports, and medical setscrews.

5. The method according to claim 1, wherein the mussel adhesive protein is a polypeptide selected from the group consisting of a peptide comprising 1 to 10 repeats of the amino acid sequence of SEQ ID NO: 1 and a peptide consisting of an amino acid sequence of SEQ ID NO: 2.

6. The method according to claim 1, wherein the mussel adhesive protein is a peptide consisting of an amino acid sequence of SEQ ID NO: 3.

7. The method according to claim 1, wherein the silica-binding peptide is one or more selected from the group consisting of amino acid sequences of SEQ ID NO: 4, SEQ ID NO: 5, SEQ ID NO: 6, and SEQ ID NO: 7.

* * * * *

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: fp-1

<400> SEQUENCE: 1

Ala Lys Pro Ser Tyr Pro Pro Thr Tyr Lys
 1               5                  10

<210> SEQ ID NO 2
<211> LENGTH: 74
<212> TYPE: PRT
<213> ORGANISM: Artificial Sequence
<220> FEATURE:
<223> OTHER INFORMATION: fp-5

<400> SEQUENCE: 2

Ser Glu Glu Tyr Lys Gly Gly Tyr Tyr Pro Gly Asn Thr Tyr His Tyr
 1               5                  10                  15
```

```
His Ser Gly Gly Ser Tyr His Gly Ser Gly Tyr His Gly Gly Tyr Lys
            20                  25                  30

Gly Lys Tyr Tyr Gly Lys Ala Lys Tyr Tyr Tyr Lys Tyr Lys Asn
        35                  40                  45

Ser Gly Lys Tyr Lys Tyr Leu Lys Lys Ala Arg Lys Tyr His Arg Lys
    50                  55                  60

Gly Tyr Lys Lys Tyr Tyr Gly Gly Ser Ser
65                  70

<210> SEQ ID NO 3
<211> LENGTH: 201
<212> TYPE: PRT
<213> ORGANISM: Artificial Sequence
<220> FEATURE:
<223> OTHER INFORMATION: fp-151

<400> SEQUENCE: 3

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Pro Trp Ser
    50                  55                  60

Ser Glu Glu Tyr Lys Gly Gly Tyr Tyr Pro Gly Asn Thr Tyr His Tyr
65                  70                  75                  80

His Ser Gly Gly Ser Tyr His Gly Ser Gly Tyr His Gly Gly Tyr Lys
                85                  90                  95

Gly Lys Tyr Tyr Gly Lys Ala Lys Tyr Tyr Tyr Lys Tyr Lys Asn
            100                 105                 110

Ser Gly Lys Tyr Lys Tyr Leu Lys Lys Ala Arg Lys Tyr His Arg Lys
        115                 120                 125

Gly Tyr Lys Lys Tyr Tyr Gly Gly Ser Gly Ser Ala Lys Pro Ser
    130                 135                 140

Tyr Pro Pro Thr Tyr Lys Ala Lys Pro Ser Tyr Pro Pro Thr Tyr Lys
145                 150                 155                 160

Ala Lys Pro Ser Tyr Pro Pro Thr Tyr Lys Ala Lys Pro Ser Tyr Pro
                165                 170                 175

Pro Thr Tyr Lys Ala Lys Pro Ser Tyr Pro Pro Thr Tyr Lys Ala Lys
            180                 185                 190

Pro Ser Tyr Pro Pro Thr Tyr Lys Leu
        195                 200

<210> SEQ ID NO 4
<211> LENGTH: 19
<212> TYPE: PRT
<213> ORGANISM: Artificial Sequence
<220> FEATURE:
<223> OTHER INFORMATION: R5

<400> SEQUENCE: 4

Ser Ser Lys Lys Ser Gly Ser Tyr Ser Gly Ser Lys Gly Ser Lys Arg
1               5                   10                  15

Arg Ile Leu

<210> SEQ ID NO 5
```

```
<211> LENGTH: 12
<212> TYPE: PRT
<213> ORGANISM: Artificial Sequence
<220> FEATURE:
<223> OTHER INFORMATION: pep1

<400> SEQUENCE: 5

Lys Ser Leu Ser Arg His Asp His Ile His His His
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Si4-1

<400> SEQUENCE: 6

Met Ser Pro His Pro His Pro Arg His His His Thr
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Si4-10

<400> SEQUENCE: 7

Arg Gly Arg Arg Arg Leu Ser Cys Arg Leu Leu
 1               5                  10

<210> SEQ ID NO 8
<211> LENGTH: 103
<212> TYPE: DNA
<213> ORGANISM: Artificial Sequence
<220> FEATURE:
<223> OTHER INFORMATION: Forward for R5

<400> SEQUENCE: 8
gcgccatatg agcagcaaaa aatctggctc ctattcaggc tcgaaaggtt ctaaacgtcg      60
cattctgggt ggcggagggg cgaaaccgag ctatccgccg acc                      103

<210> SEQ ID NO 9
<211> LENGTH: 34
<212> TYPE: DNA
<213> ORGANISM: Artificial Sequence
<220> FEATURE:
<223> OTHER INFORMATION: Reverse for MAP

<400> SEQUENCE: 9
gcgcctcgag cttgtacgtt ggaggataag aagg                                 34
```